(12) United States Patent
Gupta et al.

(10) Patent No.: US 11,990,246 B2
(45) Date of Patent: May 21, 2024

(54) IDENTIFYING PATIENTS UNDERGOING TREATMENT WITH A DRUG WHO MAY BE MISIDENTIFIED AS BEING AT RISK FOR ABUSING THE TREATMENT DRUG

(71) Applicant: Health Solutions Research, Inc., Rockville, MD (US)

(72) Inventors: Ajay Kumar Gupta, Potomac, MD (US); Ramani Peruvemba, McLean, VA (US)

(73) Assignee: HEALTH SOLUTIONS RESEARCH, INC., Rockville, MD (US)

( * ) Notice: Subject to any disclaimer, the term of this patent is extended or adjusted under 35 U.S.C. 154(b) by 1351 days.

(21) Appl. No.: 16/126,537

(22) Filed: Sep. 10, 2018

(65) Prior Publication Data
US 2020/0005948 A1    Jan. 2, 2020

Related U.S. Application Data

(63) Continuation-in-part of application No. 16/024,387, filed on Jun. 29, 2018, now Pat. No. 11,177,040.

(51) Int. Cl.
*G16H 70/40*    (2018.01)
*G16H 10/60*    (2018.01)
(Continued)

(52) U.S. Cl.
CPC ............. *G16H 70/40* (2018.01); *G16H 10/60* (2018.01); *G16H 50/30* (2018.01); *G16H 70/20* (2018.01); *G16H 70/60* (2018.01)

(58) Field of Classification Search
CPC ........ G16H 70/40; G16H 10/60; G16H 50/30; G16H 70/20; G16H 70/60
See application file for complete search history.

(56) References Cited

U.S. PATENT DOCUMENTS

| 8,758,238 B2 | 6/2014 | Clapp |
| 9,152,918 B1 | 10/2015 | McNair |

(Continued)

FOREIGN PATENT DOCUMENTS

WO    2016/172614    10/2016

OTHER PUBLICATIONS

Chen et al., "Reality mining: A prediction algorithm for disease dynamics based on mobile big data," Information Sciences 379 (2017) 82-93 (Year: 2017) ; Cited in Notice of Allowance issued in U.S. Appl. No. 16/024,387.

(Continued)

*Primary Examiner* — Jessica Lemieux
*Assistant Examiner* — William T. Monticello
(74) *Attorney, Agent, or Firm* — HSML, P.C.

(57) ABSTRACT

Patients being treated successfully with a drug of abuse and at low risk for abusing the drug nevertheless may be at high risk of being misidentified as a high risk of abuse. These patients may need and benefit from treatment with the drug but restricted or cut off from the treatment altogether due to the misidentification and then abandoned. Evaluating a patient's risk of drug treatment change due to a category misidentification may include developing a model for identifying such abandoned patients, applying the model to data of a patient, and determining a patient risk score for the patient based on a result of applying the model.

18 Claims, 8 Drawing Sheets

(51) Int. Cl.
  *G16H 50/30*  (2018.01)
  *G16H 70/20*  (2018.01)
  *G16H 70/60*  (2018.01)

(56) References Cited

U.S. PATENT DOCUMENTS

| | | |
|---|---|---|
| 2002/0183965 A1 | 12/2002 | Gogolak |
| 2005/0131740 A1 | 6/2005 | Massenzio et al. |
| 2005/0203773 A1 | 9/2005 | Soto et al. |
| 2006/0129427 A1 | 6/2006 | Wennberg |
| 2008/0091471 A1 | 4/2008 | Michon et al. |
| 2008/0228824 A1 | 9/2008 | Kenedy et al. |
| 2009/0216564 A1 | 8/2009 | Rosenfeld |
| 2011/0288886 A1* | 11/2011 | Whiddon et al. |
| 2013/0185097 A1 | 7/2013 | Saria et al. |
| 2013/0197942 A1 | 8/2013 | Chiu |
| 2013/0339053 A1 | 12/2013 | Jacobs et al. |
| 2014/0081652 A1* | 3/2014 | Klindworth |
| 2014/0236668 A1 | 8/2014 | Young et al. |
| 2015/0064137 A1 | 3/2015 | Lichtsteiner et al. |
| 2015/0213225 A1* | 7/2015 | Amarasingham et al. |
| 2015/0242586 A1 | 8/2015 | Kagen |
| 2016/0110512 A1 | 4/2016 | Adjaoute |
| 2016/0314256 A1 | 10/2016 | Su et al. |
| 2016/0316723 A1 | 11/2016 | Wall et al. |
| 2016/0378932 A1 | 12/2016 | Sperling et al. |
| 2017/0004275 A1* | 1/2017 | Mehta et al. |
| 2017/0061077 A1 | 3/2017 | Cline et al. |
| 2017/0076058 A1 | 3/2017 | Stong |
| 2017/0103172 A1 | 4/2017 | Fink et al. |
| 2017/0109493 A1 | 4/2017 | Hogg et al. |
| 2017/0132371 A1 | 5/2017 | Amarasingham et al. |
| 2017/0199979 A1 | 7/2017 | Reiner |
| 2017/0286622 A1 | 10/2017 | Cox et al. |
| 2017/0351834 A1 | 12/2017 | Cahan et al. |
| 2018/0137235 A1* | 5/2018 | Meshkin |
| 2018/0330824 A1* | 11/2018 | Athey et al. |
| 2018/0366221 A1 | 12/2018 | Crehore et al. |
| 2019/0088356 A1 | 3/2019 | Oliver et al. |
| 2019/0133536 A1 | 5/2019 | Roberts et al. |
| 2019/0182749 A1 | 6/2019 | Breaux et al. |
| 2019/0272925 A1 | 9/2019 | Barrett et al. |
| 2020/0225189 A1 | 7/2020 | Verma et al. |
| 2020/0294680 A1 | 9/2020 | Gupta et al. |
| 2020/0349324 A1 | 11/2020 | Ostby et al. |
| 2021/0166819 A1 | 6/2021 | Gupta et al. |
| 2021/0319884 A1 | 10/2021 | Day et al. |
| 2021/0366621 A1 | 11/2021 | Miff et al. |
| 2022/0059242 A1 | 2/2022 | Schneider et al. |
| 2023/0070131 A1 | 3/2023 | Frieder et al. |

OTHER PUBLICATIONS

Chang et al., "Mobility network models of COVID-19 explain inequities and inform reopening", Nature, vol. 589, 44 pages, Nov. 10, 2020, available at https://www.nature.com/articles/s41586-020-2923-3.

\* cited by examiner

IDENTIFYING PATIENTS UNDERGOING TREATMENT WITH A DRUG WHO MAY BE MISIDENTIFIED AS BEING AT RISK FOR ABUSING THE TREATMENT DRUG

CROSS-REFERENCE TO RELATED APPLICATION

This application is a continuation-in-part of U.S. patent application Ser. No. 16/024,387, filed on Jun. 29, 2018, the entire disclosure of which is hereby incorporated by reference herein.

TECHNICAL FIELD

The present disclosure relates to a data analytic approach to providing point-of-care decision support to clinicians and, in one or more embodiments, to identifying patients undergoing treatment with a drug who may be misidentified as being at risk for abuse of the drug.

BACKGROUND

Healthcare has advanced by leaps and bounds and technology has the potential to drive further advancement, for example through the use of data and informatics to derive clinical insights leading to improved quality of patient care.

Addiction to pain killers has many contributing root causes that are influenced by many factors. For example, opioid addiction may be influenced by factors such as the different types of opioids or narcotics (including legally prescribed opioids, illegally diverted prescribed opioids, and illegal opioids such as heroin or illegally manufactured fentanyl) or the numerous sources of opioids, both licit and illicit (including physician's offices, pharmacies, hospitals, behavioral health clinics, or the variety of illegal sources).

Risk analysis may be employed to identify risks and populations subject to such risks, and to correlate the risks to the subject population in accordance with various factors. One such example is the identification of people as belonging to a category of those being at risk for drug dependence or addiction, of which opioid addiction is a rapidly growing problem. Results of risk analysis have led to restricting patient access to opioid painkillers, such as through policy or guidance limiting the length of a prescription (in some cases to as low as three days) or the dosage of the prescription. As a result, in some cases patients on a long-term opioid regimen have had their coverage cancelled by their insurance provider or been forced to taper off their medication. Patients who experience episodic pain also suffer as they are often seen as exhibiting drug-seeking behavior.

While efforts to reduce opioid prescriptions are helpful and appropriate in many cases, there are patients for whom opioid medications do provide relief from pain, whether long-term, chronic, or episodic. Left without their prescription medication, these patients may feel abandoned, fall into depression, resort to illegal narcotics, and in the worst cases take their own lives. While an exact number of these impacted "abandoned patients" is not known, patients on long-term opioid treatment are believed to account for a substantial portion.

No approach exists that effectively identifies an individual who is benefited by ongoing treatment but at risk of such treatment being modified or discontinued due to factors shared with the population at large who are at risk of substance abuse.

SUMMARY

In a first aspect, a method to evaluate a patient's risk of drug treatment change due to a category misidentification may comprise acquiring data of a subject population (X); identifying patients (Y) as a first subset of the subject population (X) based on at least one criterion; identifying patients (Z) as a second subset of the subject population (X) based on a model; determining a correlation between (Y) and (Z); determining whether the correlation at least meets a predetermined threshold; if the correlation does not at least meet the threshold, adjusting the model and repeating identifying patients (Z), determining a correlation between (Y) and (Z), and determining whether the correlation at least meets a predetermined threshold in accordance with the adjustment; if the correlation at least meets the threshold, outputting the model; applying the model to data of a patient; and determining a patient risk score for the patient based on a result of the applying.

In a second aspect, a method to evaluate a patient's risk of drug treatment change due to a category misidentification may comprise: determining a patient's risk of abuse of a painkilling drug based on a model; determining whether the patient's risk of abuse of the painkilling drug is relatively high or relatively low based on a standard; if the patient's risk of abuse of the painkilling drug is determined to be relatively low, indicating referral of the patient for treatment with the painkilling drug; outputting the model; applying the model to data of a patient; and determining a patient risk score for the patient based on a result of the applying.

In a third aspect, a non-transitory computer-readable medium having computer-readable instructions that, if executed by a computing device, cause the computing device to perform operations comprise: acquiring data of a population (X); identifying patients (Y) as a first subset of population (X) based on at least one criterion; identifying patients (Z) as a second subset of population (X) based on a model; determining a correlation between (Y) and (Z); determining whether the correlation at least meets a predetermined threshold; if the correlation does not at least meet the threshold, adjusting the model and repeat identifying patients (Z), determining a correlation between (Y) and (Z), and determining whether the correlation at least meets a predetermined threshold in accordance with the adjustment; if the correlation at least meets the threshold, outputting the model; applying the model to data of a patient; and determining a patient risk score for the patient based on a result of the applying.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1A:
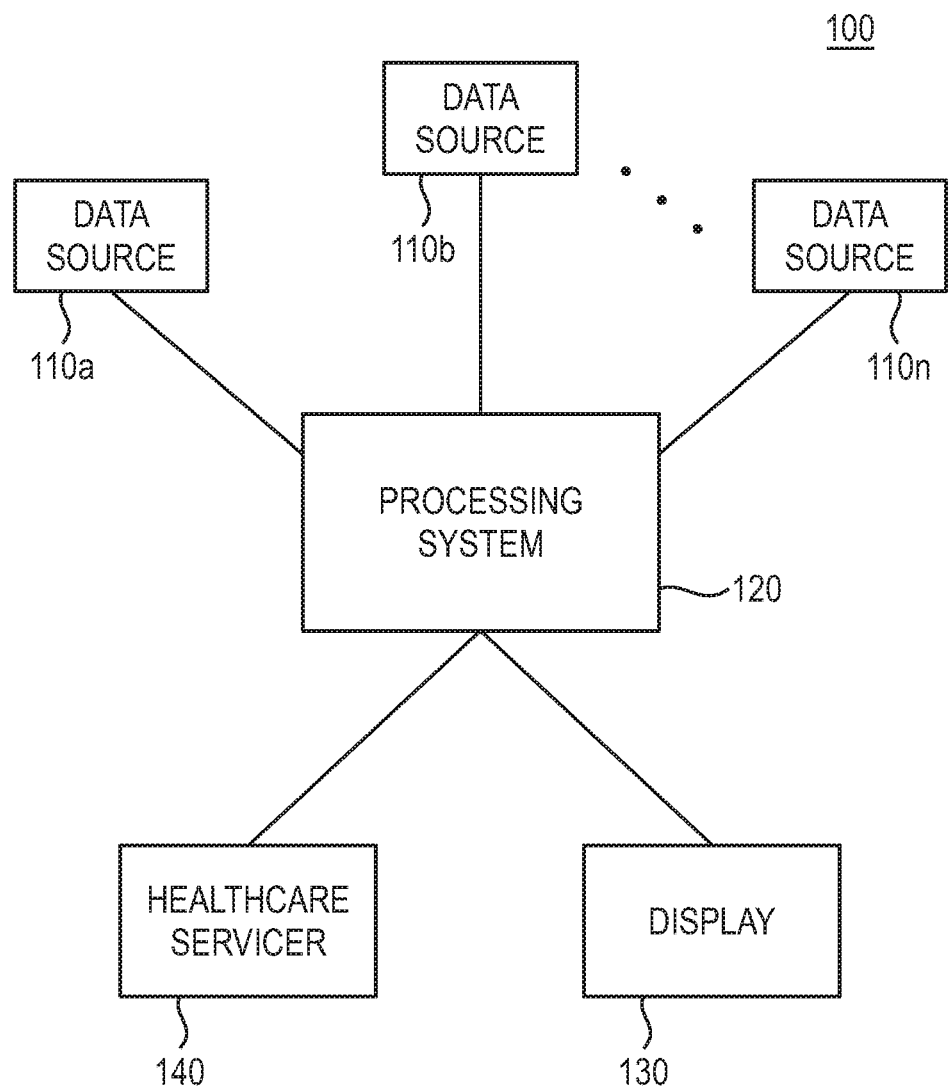
FIG. 1A shows an example configuration of a system in which identification of abandoned patients may be implemented, arranged in accordance with at least some embodiments described herein.

In the following detailed description, reference is made to the accompanying drawings, which form a part of the description. In the drawings, similar symbols typically identify similar components, unless context dictates otherwise. Furthermore, unless otherwise noted, the description of each successive drawing may reference features from one or more of the previous drawings to provide clearer context and a more substantive explanation of the current example embodiment. Still, the example embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein and illustrated in the drawings, may be arranged, substituted, combined, separated, and designed in a wide variety of different configurations, all of which are explicitly contemplated herein.

In some embodiments presented herein, the data analysis may provide clinical insights relevant to the point-of-care that allows for lower system costs and improved care and/or care delivery for subjects being successfully treated with a drug, individually or as part of a larger regimen, but misidentified as at risk for abuse of the drug. The approach described herein has broad relevance in everyday care. In addition, the approach may address more urgent needs, for example in instances of declared public health emergencies and/or areas of high cost driven by, e.g., an uncontrolled medical condition and/or expanding illness, examples of which may include the opioid epidemic, long term diabetes management, or other specific use case within an area that responds to a current healthcare challenge. For purposes of this description, the opioid crisis will serve as an example. As one of ordinary skill in the art will readily recognize, the approach may be applied to other health challenges including but not limited to those specifically mentioned herein.

FIG. 1A shows an example configuration of a system 100 in which identification of the abandoned patient may be implemented, arranged in accordance with at least some embodiments described herein. FIG. 1A shows a plurality of data sources 110a, 110b, . . . 110n (collectively, "data sources 110" hereafter), which may be communicatively coupled to a processing system 120. Processing system 120 may be communicatively coupled to a display 130 and a health care servicer 140 (e.g., a hospital or other point-of-care provider). By way of example and without limitation, one or more of the communicative couplings may be wired or wireless connections as would be understood by one of ordinary skill in the art.

In the context of drug treatment, examples of information that data sources 110 may provide may include, but are not limited to, information related to one or more of overdose and/or suicide attempts and fatalities (which, for example, may be obtained from the Centers for Disease Control); patients who had been under long-term pain management treatment which was tapered off or discontinued (obtained, for example, from insurance and Medicare claims, and/or from structured and unstructured health data (e.g., clinician's notes or discharge summaries) and/or from EHR (electronic health record) systems). These and other data may be obtained from other sources, and in the future additional sources of such data may become available and used as well.

Figure 1B:
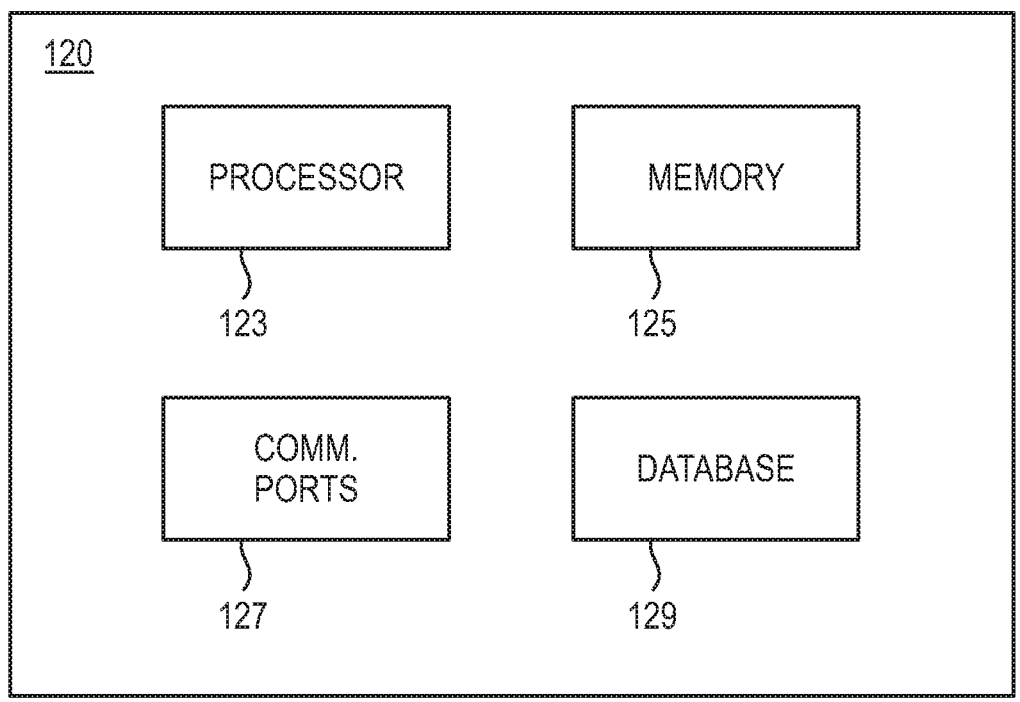
FIG. 1B shows an example configuration of a processing system that may be implemented, arranged in accordance with at least some embodiments described herein.

FIG. 1B shows an example configuration of a processing system 120 that may be implemented, arranged in accordance with at least some embodiments described herein. In one or more embodiments, processing system 120 may include one or more processors or computing devices 123 (collectively, "processor" as used herein), a system memory 125, communication ports 127 to acquire data from one or more of data sources 110, and a database 129. Processing system 120 may be configured and arranged to implement an information system platform with a data analytic engine as discussed below. Data acquired from data sources 110 may be added to database 129. The stored data may be analyzed using data analytics and formatted for output for any suitable purpose, such as for further analysis or review (e.g., personal or machine) either locally or remotely (e.g., into the EHR system at a hospital or other healthcare setting 140).

The model described herein and implemented by processing system 120 is presented, without limitation, as a bifurcated model around the out-patient (e.g., long-term, chronic pain) and the in-hospital (e.g., intense, episodic pain) settings as patients in these settings will present differently.

Outpatient Setting

Figure 2:
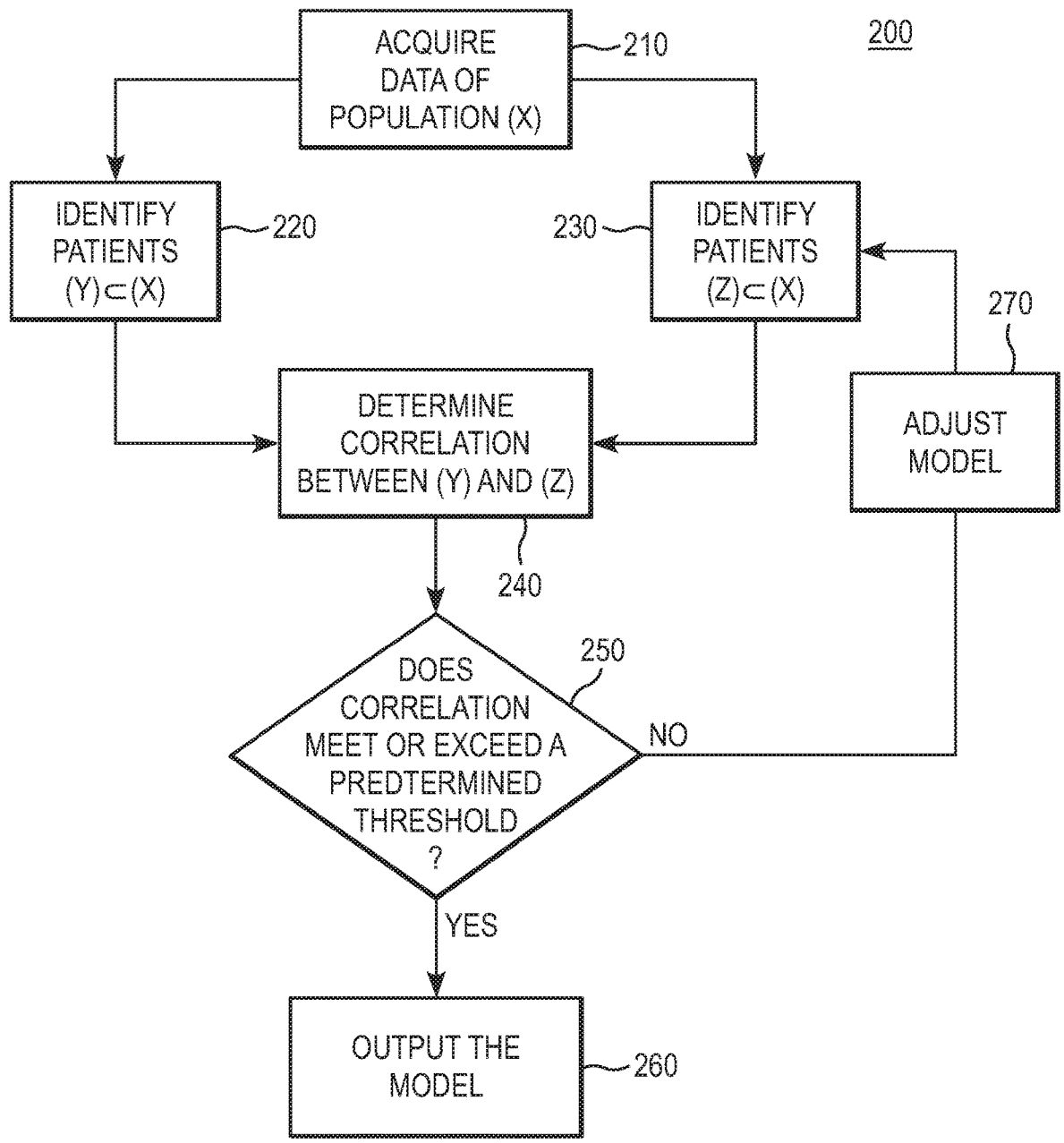
FIG. 2 shows an example processing flow by which a model to identify abandoned patients in an outpatient setting may be developed, arranged in accordance with at least some embodiments described herein.

FIG. 2 shows an example processing flow 200 by which a model to identify abandoned patients in an outpatient setting may be developed, arranged in accordance with at least some embodiments described herein. In one or more embodiments, the model uses general population data to identify patients at low risk for an opioid abuse disorder and at high risk of abandonment, patients who need and benefit from opioid medication for treatment of, e.g., long-term, chronic pain.

Processing flow 200 may include one or more operations, actions, or functions depicted by one or more blocks 210, 220, 230, 240, 250, 260, and 270. Although illustrated as discrete blocks, various blocks may be divided into additional blocks, combined into fewer blocks, or eliminated, depending on the desired implementation. As a non-limiting example, the description of processing flow 200, corresponding to the depiction thereof in FIG. 2 and performed by processing system 120 in one or more embodiments described herein, pertains to identifying abandoned patients in an outpatient setting. Processing may begin at block 210.

Block 210 (Acquire Data of Population (X)) may refer to processing system 120 receiving data of a subject population (X) from data sources 110 via communication ports 127. Subject population (X) may include victims of e.g., overdose, suicide attempt, and/or suicide fatality over a period of time data may be acquired in one or more of a variety of ways, including but not limited to wireless or wired communications from data sources 110 or manual entry (for example, by an operator using a keyboard or tablet, smartphone, etc. utilizing appropriate application software). In some embodiments, and without limitation, the data of subject population (X) may be obtained from public sources such as the Centers for Disease Control. Block 210 may be followed by Block 220 and Block 230.

Block 220 (Identify Patients (Y) in (X)) may refer to processor 123 identifying a subset (Y) of subject population (X) in which (Y) includes patients who had been under long-term pain management treatment which was tapered off or discontinued before their overdoses, suicide attempts, or suicide fatalities, in the examples given. It is considered that subset (Y) may include a statistically significant percentage of abandoned patients. This data may be obtained from insurance (including Medicare) claims, by way of nonlimiting example.

Block 230 (Identify Patients (Z) in (X)) may refer to processor 123 applying a model in performing a retrospective analysis of the risk level of subject population (X) to identify patients in subject population (X) who may have been misidentified as being at risk of abusing their drug of treatment. For example, the model may produce a risk score for each individual in the subject population (X) and identify those individuals (Z) who would not be considered at risk for abuse of their drug.

In one or more embodiments, the model may have a plurality of analyzer channels, each of which corresponds to an observable condition of a patient. The channels may be weighted to customize or fine tune the model, signifying whether any channels are of equal or greater/lesser importance than others in identifying an abandoned patient.

Predictive modeling may allow allocation of channel points in accordance with or independently of channel weighting, based on the statistical sensitivity of specific factors in predicting, for example, abandoned patients. For example, a base score may be calculated as the summation of points attributed to the (weighted or unweighted) analyzer channels. The analyzer channels may be broken down further into analyzer features that provide additional sensitivity in identifying individuals at high risk of misidentification and abandonment.

The following Table shows but one example of a model in which analyzer channels may be assigned to various factors influencing the base score. In one or more embodiments, points and/or weights may be assigned to each channel. The Table includes narrative information of each channel individually in the example, including examples of features that may be used for each channel. It should be noted that not all of the included channels or features need be part of any given analysis. Moreover, other channels and/or features may be suitable in addition or in the alternative, depending on the study or analysis. In one or more embodiments, point modifiers may be applied to one or more of the channels and/or features to affect the influence of the same on the total base score. Nonlimiting examples include percentage weightings, inclusion/exclusion of certain channels/features to suit any particular analysis or subject population, etc.

| Channel | Criteria |
| --- | --- |
| Tolerance | Stable dose, long-term |
| Dosage | Stable dosage |
| Withdrawal | No evidence of withdrawal symptoms |
| Drug Seeking Behavior | Same provider or provider group |
| Diversion | Same pharmacy |
| Overdose | No reported overdose |

In one or more embodiments, the model may place a higher weight or point value for any or all of the channels. In other words, whether certain conditions place a patient at greater risk for abandonment in a long-term chronic pain management setting than other chronic pain conditions may be considered. For example, whether a high, long-term stable dose is worse than a low or medium long-term stable dose (and have a corresponding weight or point value) from the perspective of a patient developing an addiction may be considered in the model. In a sense, this may be the answer to the question: Should all long-term chronic care patients be tapered to a lower opioid equivalent dose for pain management? Block 220 and 230 may be followed by Block 240.

Block 240 (Determine Correlation Between (Y) and (Z)) may refer to processor 123 determining a correlation between patients (Y) identified in Block 220 and patients (Z) identified in Block 230. The correlation may be any suitable correlation that results in a value that can be compared to a threshold value. For example, in one or more embodiments, processor 123 may calculate a mathematical correlation between patients (Y) and patients (Z). Additionally or alternatively, in one or more embodiments, processor 123 may determine which individuals in (Y) are also in (Z) and compare the result to a threshold. Block 240 may be followed by Block 250.

Block 250 (Does Correlation Meet or Exceed a Predetermined Threshold?) may refer to processor 123 determining whether the result of Block 240 exceeds a predetermined threshold. If so, then Block 260 may follow Block 250. If not, then Block 270 may follow Block 250.

Block 260 (Output the Model) may refer to processor 123 outputting the model for, e.g., incorporation into a healthcare records system such as EHR and the model is considered valid for implementation in determining whether a subject patient may be at risk of being an abandoned patient Block 270 (Adjust Model) may refer to one or more channels being modified, deleted, or added to the model and fed back to Block 230 for re-testing in an iterative process performed until Block 250 is answered "YES." For example, a channel may be modified by adding points or point multipliers, or by changing or adding the weighting.

The base score may be adjusted based on several variables in order to obtain a risk score used to modify a clinician's behavior, for example. In one or more embodiments, a positive adjustment may be made based on the number of total active channels as well as having channels with greater than five active analyzer features. A negative adjustment may be made for single active channels as well as for having fewer than five active features among all analyzer channels. Additional positive adjustments may be made in accordance with, e.g., NLP, for analyzer features having grammatical phrases of greater than four words. In one or more embodiments, the composite score may be the sum of the base points and adjustment points, although other combinations of these and/or other variables may be employed additionally or as modifications to the above.

For reference and by way of illustration only, with no undue limitation intended, a "channel diversity" risk point boost, such as for example 50 points, may be given per active channel, it being considered that the more active/diverse model channels, the higher probability/precision. Coincidentally, a "channel activity" boost, such as for example 25 points, may be given for every channel having greater than five markers active, presuming that the more activity in channels, the higher probability/precision. Similarly, a "4 gram+ marker" boost, such as for example 10 points, may be given for every 4-gram or greater marker active, in consideration that longer marker "phrases" (e.g., from a clinician's notes: "pt rec pain meds") may result in higher probability/precision.

On the other hand, a "single channel active point reduction", such as for example 5%-10% in total base points, may be charged on the presumption that narrower channel activity implies lower probability. Similarly, a "limited active marker point reduction", such as for example 5%-10% of total base points, may be incurred if a small number, such as fewer than five (5) active markers, are present (across all channels), it being considered that fewer markers active equates to lower probability.

Figure 3:
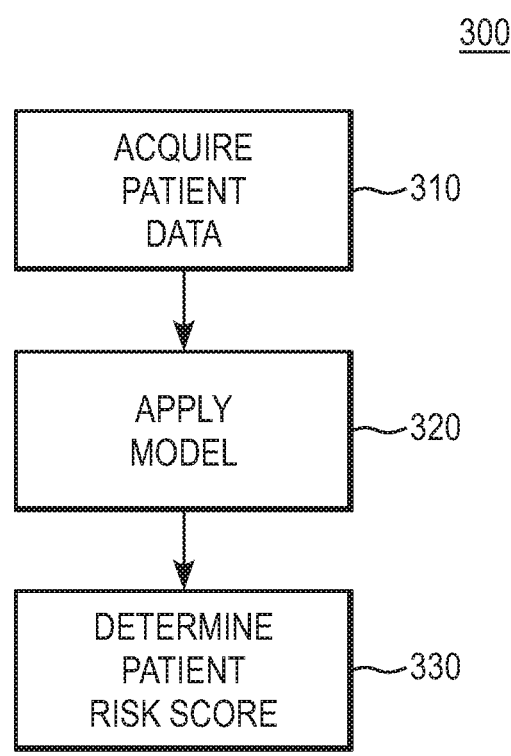
FIG. 3 shows an example processing flow by which an outpatient risk score may be obtained, arranged in accordance with at least some embodiments described herein.

FIG. 3 shows an example processing flow 300 by which an outpatient risk score may be obtained, arranged in accordance with at least some embodiments described herein. Processing flow 300 may include one or more operations, actions, or functions depicted by one or more blocks 310, 320, and 330. Although illustrated as discrete blocks, various blocks may be divided into additional blocks, combined into fewer blocks, or eliminated, depending on the desired implementation. As a non-limiting example, the description of processing flow 300, corresponding to the depiction thereof in FIG. 3 and performed by processing system 120 in one or more embodiments described herein, pertains to obtaining a patient risk score in an outpatient setting. Processing may begin at block 310.

Block 310 (Acquire Patient Data) may refer to processor 123 obtaining data of an outpatient who is being successfully treated with a drug (e.g., a painkiller such as an opioid) but at risk of being misidentified as being at risk of abusing the drug. The data acquired in Block 310 may include, without limitation, data corresponding to that of the above Table. Block 310 may be followed by Block 320.

Block 320 (Apply Model) may refer to processor 123 analyzing the data acquired in Block 310 in accordance with the model validated according to procedure 200 and outputted at Block 260. For example, the data in each analyzer channel may be converted to a channel score. Block 320 may be followed by Block 330.

Block 330 (Determine Patient Risk Score) may refer to processor 123 determining a patient risk score based on the channel scores determined in Block 320. For example, the channel scores may be summed to create a patient risk score.

The patient risk score determined in Block 320 may be interpreted automatically or by a care provider to determine whether the patient is at risk of becoming an abandoned patient. For example, at the point of care, a physician can determine from the patient risk score that a patient, who is benefiting from opioid treatment and showing no signs of abuse, need not have his dosage reduced or canceled. In some embodiments, the determination can be made on the basis of comparing the patient risk score with the base score determined in FIG. 2. The patient risk score can be utilized in other ways as well. For example and without limitation, clinician behavior (e.g., opioid prescription habits including whether a dosage increase may be justified without risk of approaching or exceeding the base score, number of opioid prescriptions written, and ordering additional monitoring or behavioral health consultation, etc.) can be compared from the year prior to implementation with the clinician behavior during implementation. This information can be fed back and considered with other empirical information to make and track changes to pain management treatment plans and measure their effectiveness, for example by incorporating this information into hospital EHR and informatics systems to assist clinicians in treating patients in clinical settings as well as post-discharge.

In-Hospital Setting

In the in-hospital setting, a patient presenting with, e.g., intense episodic pain, such as with sickle cell disease or lower back pain, are often considered drug-seeking. Such patients, without a consistent and regular history of outpatient pain management treatment, represent a different challenge. In these patients, a risk assessment based on information garnered from inpatient medical records is used to assess their overall risk profile, reflected in a patient risk score. An approach to evaluate these patients includes identifying whether they are at low risk of an opioid addiction, diversion, and/or overdose, utilizing the Opioid Abuse Related Mortality, or OARM described in U.S. patent application Ser. No. 16/024,387, the disclosure of which is hereby incorporated by reference herein. An example approach may employ the following channels:

01—RESERVED
02—MEDICAL ACTIVITY
03—CHEMICAL HEALTH
04—DIAGNOSIS
05—PAIN CONTROL
06—PAIN
07—PSYCHOLOGICAL
08—ABUSE
09—LIFESTYLE
10—FAMILY HISTORY
11—SOCIAL WORK
12—LAB TOX
13—ILLEGAL DRUGS
14—MEDICATION (NICOTINE)
15—MEDICATION (DOSE-FORM)
16—MEDICATION (ACTION)
17—MEDICATION (DETOX)

As is the case in identifying abandoned patients in the outpatient setting, points and/or weights may be assigned to each channel in the in-hospital setting. Accordingly, not all of the listed channels or features need be part of any given analysis. Moreover, other channels and/or features may be suitable in addition or in the alternative, depending on the study or analysis. In one or more embodiments, point modifiers may be applied to one or more of the channels and/or features to affect the influence of the same on the total base score. Nonlimiting examples include percentage weightings, inclusion/exclusion of certain channels/features to suit any particular analysis or subject population, etc.

Figure 4:
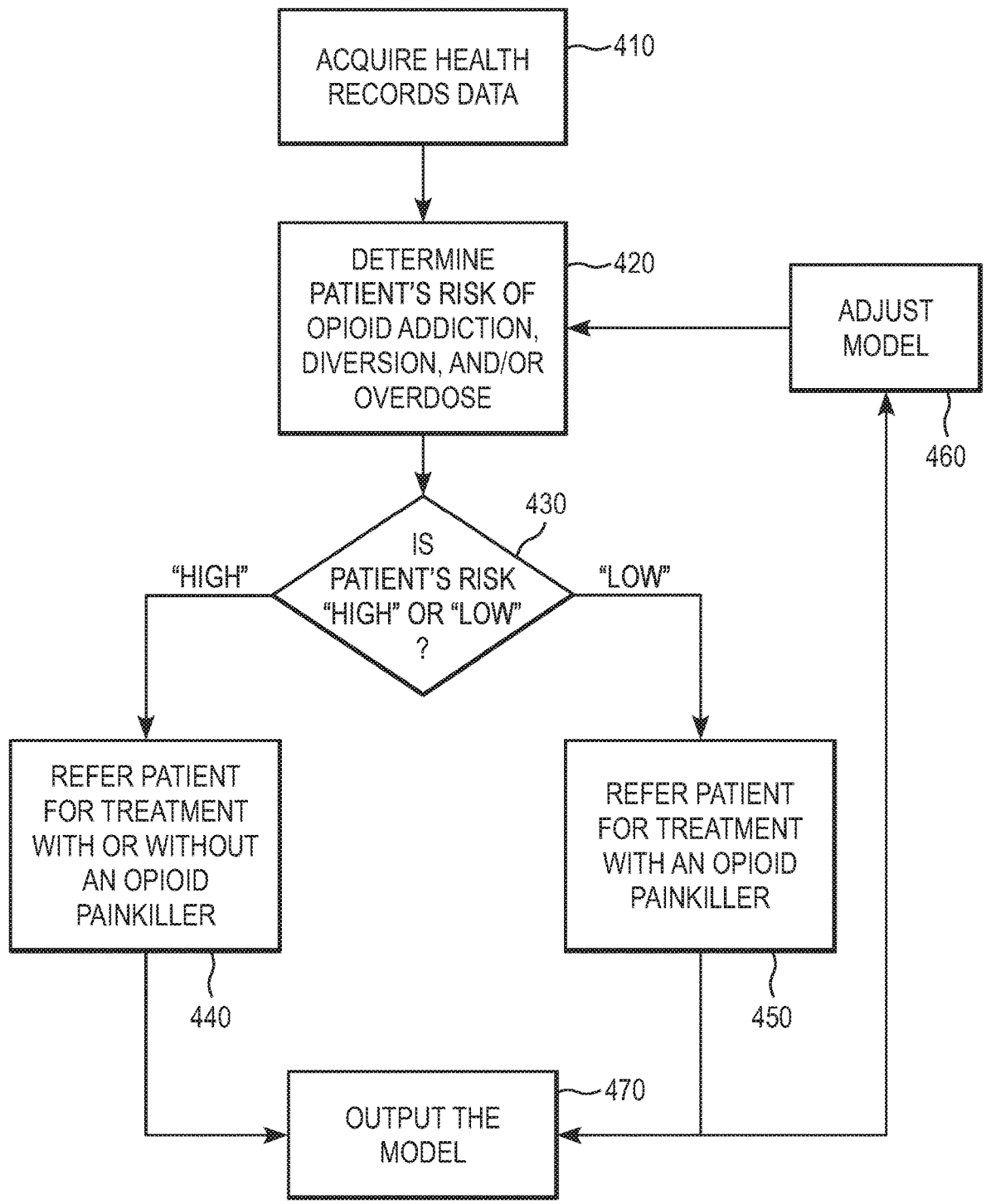
FIG. 4 shows an example processing flow by which a model to identify abandoned patients in an in-hospital setting may be developed, arranged in accordance with at least some embodiments described herein.

FIG. 4 shows an example processing flow 400 by which a model to identify abandoned patients in an in-hospital setting may be developed, arranged in accordance with at least some embodiments described herein. In one or more embodiments, the model uses data from, e.g., inpatient medical records to identify patients at low risk for an opioid abuse disorder and at high risk of abandonment, patients who need and benefit from opioid medication for treatment of, e.g., intense, episodic pain. Processing flow 400 may include one or more operations, actions, or functions depicted by one or more blocks 410, 420, 430, 440, 450, 460, and 470. Although illustrated as discrete blocks, various blocks may be divided into additional blocks, combined into fewer blocks, or eliminated, depending on the desired implementation. As a non-limiting example, the description of processing flow 400, corresponding to the depiction thereof in FIG. 4 and performed by processing system 120 in one or more embodiments described herein, pertains to obtaining a patient risk score in an outpatient setting. Processing may begin at block 410.

Block 410 (Acquire Hospital Records Data) may refer to processor 123 acquiring hospital records data, such as electronic health records (EHR) systems data. For example, the information for the channels can be extracted through a natural language processing (NLP) approach from clinician's notes as well as from structured text. Block 410 may be followed by Block 420.

Block 420 (Determine a Patient's Risk of Opioid Addiction, Diversion, and/or Overdose) may refer to processor 123 determining a patient's risk of opioid addiction, diversion, and/or overdose, utilizing the Opioid Abuse Related Mortality, or OARM described in U.S. patent application Ser. No. 16/024,387, e.g., in the in-hospital setting. For example, the patient may be scored in accordance with one or more of the analyzer channels listed above. Block 420 may be followed by Block 430.

Block 430 (Is Patient's Risk "High" or "Low" ?) may refer to processor 123 determining whether the patient is at "high" or "low" risk of opioid addiction, diversion, or overdose. For example, if in Block 420 the OARM indicates that the patient is at "high" risk of opioid addiction, diversion, and/or overdose as determined by a subjective (e.g., based on a clinician's judgment) standard and/or objective (e.g., based on a policy) standard, then Block 430 may be followed by Block 440. On the other hand, if in Block 420 the OARM indicates that the patient is at "low" risk of opioid addiction, diversion, and/or overdose as determined by the subjective and/or objective standard(s), then Block 430 may be followed by Block 450.

Block 440 (Refer Patient for Treatment With or Without an Opioid Painkiller) may refer to the patient being referred by, e.g., an attending physician, for treatment with an opioid painkiller or another painkiller, or for no medicinal treatment at all. If referred for medicinal treatment, the choice of treatment may be subject to stringent guidelines established, e.g., in response to the current opioid epidemic, such as reduced dose or duration of opioid treatment or treatment with an over-the-counter NSAID painkiller. Appropriate monitoring of the patient's response may be indicated as well. Block 440 may be followed by Block 470.

Block 450 (Refer Patient for Treatment With an Opioid Painkiller) may refer to the patient being referred for treatment with an opioid painkiller and identified as a potential abandoned patient. For example, the patient may be prescribed a dosage that is more liberal (e.g., in accord with dosages prescribed for similar patients before current stringent guidelines were instituted) than a dosage that might be restricted for a patient at the "high" risk level. Appropriate monitoring of the patient's response may be indicated as well. Block 450 may be followed by Block 460 and by Block 470.

Block 460 (Adjust Model) may refer to processor 123 modifying, deleting, or adding one or more channels to the model and feeding back to Block 420 in an iterative process. For example, the adjustments may be made by a clinician based on feedback from monitoring patients undergoing treatment in accordance with the OARM model, such as by adding points or point multipliers, or by changing or adding the weighting of one or more channels. Block 460 may be followed by Block 420.

Block 470 (Output Model) may refer to processor 123 outputting the model for deployment in a healthcare records system such as the EHR system. For example, the model may be utilized in accordance with a patient's record to determine a patient risk score at the point of care as an aid to determining a course of treatment.

Figure 5:
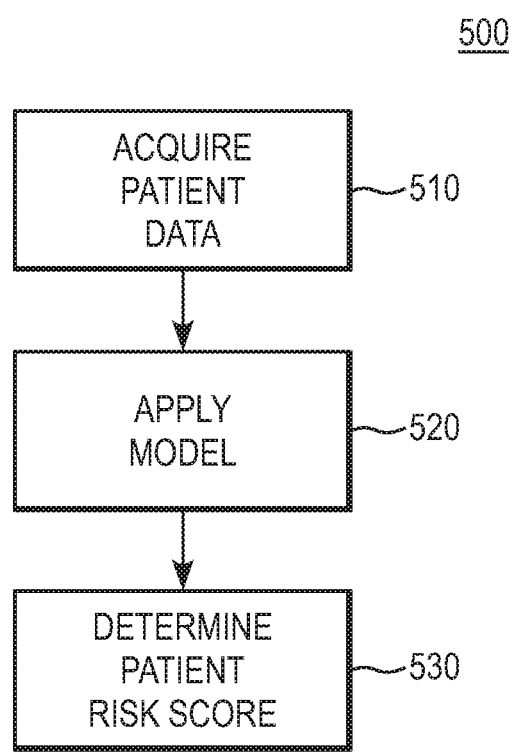
FIG. 5 shows an example processing flow by which an in-hospital patient risk score may be obtained, arranged in accordance with at least some embodiments described herein.

FIG. 5 shows an example processing flow 500 by which an in-hospital patient risk score may be obtained, arranged in accordance with at least some embodiments described herein. Processing flow 500 may include one or more operations, actions, or functions depicted by one or more blocks 510, 520, and 530. Although illustrated as discrete blocks, various blocks may be divided into additional blocks, combined into fewer blocks, or eliminated, depending on the desired implementation. As a non-limiting example, the description of processing flow 500, corresponding to the depiction thereof in FIG. 5 and performed by processing system 120 in one or more embodiments described herein, pertains to obtaining a patient risk score in an in-hospital setting. Processing may begin at block 510.

Block 510 (Acquire Patient Data) may refer to processor 123 obtaining data of an in-hospital patient who is being successfully treated with a drug (e.g., a painkiller such as an opioid) but at risk of being misidentified as being at risk of abusing the drug. The data acquired in Block 510 may include, without limitation, data from EHR records. Block 510 may be followed by Block 520.

Block 520 (Apply Model) may refer to processor 123 analyzing the data acquired in Block 510 in accordance with the model validated according to procedure 200. For example, the data in each analyzer channel may be converted to a channel score. Block 520 may be followed by Block 530.

Block 530 (Determine Patient Risk Score) may refer to processor 123 determining a patient risk score based on the channel scores determined in Block 520. For example, the channel scores may be summed to create a patient risk score. This risk score can be interpreted in accordance with the "high" and "low" risk standards. For example, patients identified as low risk of overdose, diversion, and/or addiction may be identified as potential abandoned patients and treated as described above. On the other hand, patients identified as high risk are less likely to become abandoned patients and are thus treated as described above.

In order to customize and improve application of either the outpatient model or in-hospital model, clinician behavior (e.g., opioid prescription habits including total opioid prescriptions written, and ordering additional monitoring or behavioral health consultation, etc.) can be compared from the year prior to implementation with the clinician behavior during implementation. This information can be fed back and considered with other empirical information to make and track changes to pain management treatment plans and measure their effectiveness, for example by incorporating the model into hospital EHR and informatics systems to assist clinicians in treating patients in hospital settings as well as post-discharge.

Figure 6:
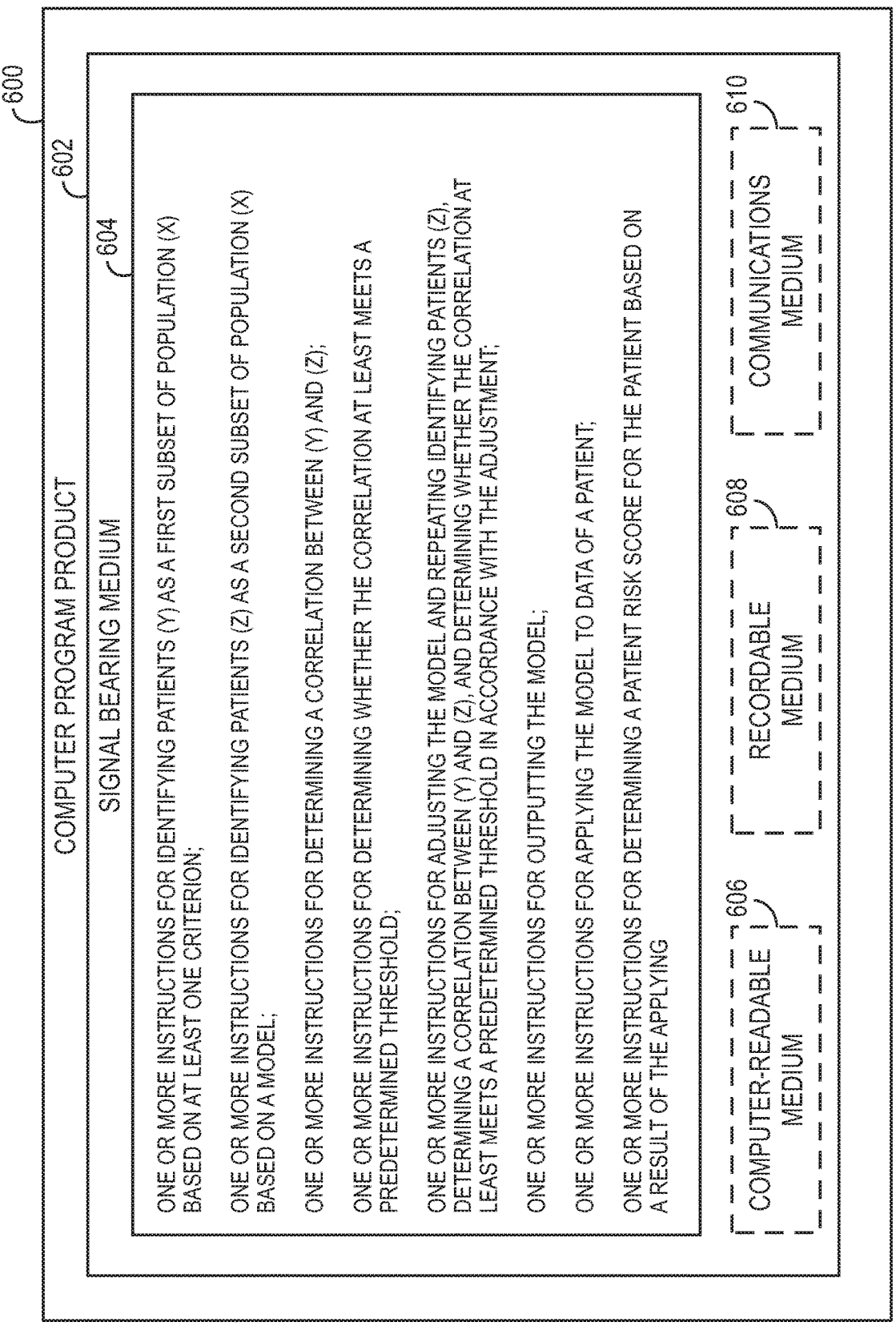
FIG. 6 illustrates computer program products that may be utilized to provide a scheme for identifying abandoned patients, arranged in accordance with at least some embodiments described herein.

FIG. 6 illustrates computer program products that may be utilized to provide a scheme for identifying abandoned patients, arranged in accordance with at least some embodiments described herein. Program product 600 may include a signal bearing medium 602. Signal bearing medium 602 may include one or more instructions 604 that, when executed by, for example, a processor, may provide the functionality described above with respect to FIGS. 1A-S. By way of example, but not limitation, instructions 604 may include: one or more instructions for identifying patients (Y) as a first subset of population (X) based on at least one criterion; one or more instructions for identifying patients (Z) as a second subset of population (x) based on a model; one or more instructions for determining a correlation between (Y) and (Z); one or more instructions for determining whether the correlation at least meets a predetermined threshold; one or more instructions for adjusting the model and repeating identifying patients (Z), determining a correlation between (Y) and (Z), and determining whether the correlation at least meets a predetermined threshold in accordance with the adjustment; one or more instructions for outputting the model; one or more instructions for applying the model to data of a patient; one or more instructions for determining a patient risk score for the patient based on a result of the applying. Thus, for example, referring to FIGS. 2-5, processor 123 may undertake one or more of the blocks shown in FIGS. 2-5 in response to instructions 604.

In some implementations, signal bearing medium 602 may encompass a computer-readable medium 606, such as, but not limited to, a hard disk drive, a CD, a DVD, a digital tape, memory, etc. In some implementations, signal bearing medium 602 may encompass a recordable medium 608, such as, but not limited to, memory, read/write (R/W) CDs, R/W DVDs, etc. In some implementations, signal bearing medium 602 may encompass a communications medium 610, such as, but not limited to, a digital and/or an analog communication medium (e.g., a fiber optic cable, a waveguide, a wired communications link, a wireless communication link, etc.). Thus, for example, computer program product 600 may be conveyed to one or more modules of processor 123 by an RF signal bearing medium, where the signal bearing medium is conveyed by a wireless communications medium (e.g., a wireless communications medium conforming with the IEEE 802.11 standard).

Figure 7:
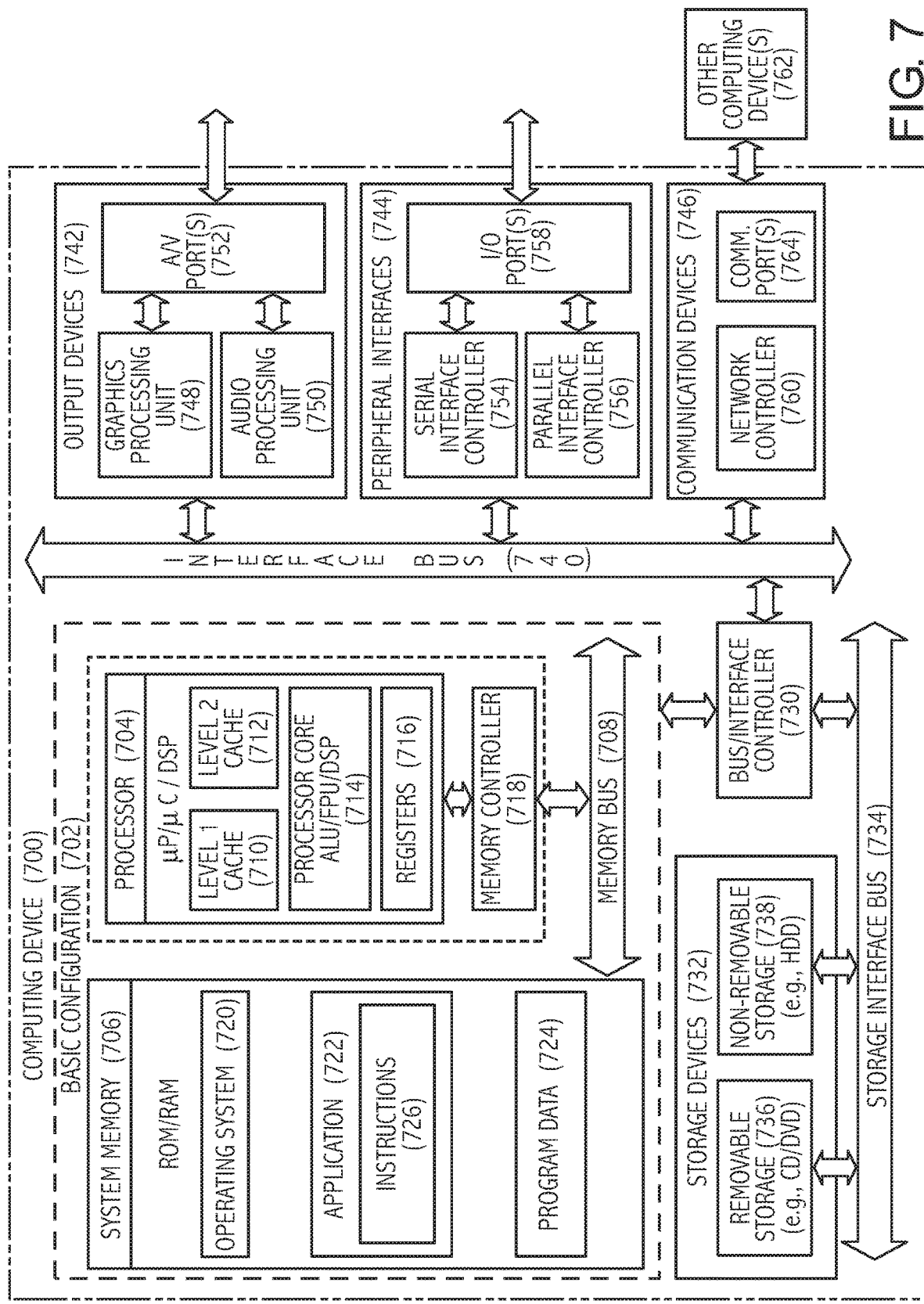
FIG. 7 shows a block diagram illustrating an example computing device 700 by which various example solutions described herein may be implemented, arranged in accordance with at least some embodiments described herein.

FIG. 7 shows a block diagram illustrating an example computing device 700 by which various example solutions described herein may be implemented, arranged in accordance with at least some embodiments described herein. In a very basic configuration 702, computing device 700 typically includes one or more processors 704 and a system memory 706. A memory bus 708 may be used for communicating between processor 704 and system memory 706.

Depending on the desired configuration, processor 704 may be of any type including but not limited to a microprocessor (VIP), a microcontroller (IC), a digital signal processor (DSP), or any combination thereof. Processor 704 may include one more levels of caching, such as a level one cache 710 and a level two cache 712, a processor core 714, and registers 716. An example processor core 714 may include an arithmetic logic unit (ALU), a floating point unit (FPU), a digital signal processing core (DSP Core), or any combination thereof. An example memory controller 718 may also be used with processor 704, or in some implementations memory controller 718 may be an internal part of processor 704.

Depending on the desired configuration, system memory 706 may be of any type including but not limited to volatile memory (such as RAM), non-volatile memory (such as ROM, flash memory, etc.) or any combination thereof. System memory 706 may include an operating system 720, one or more applications 722, and program data 724. Application 722 may include instructions 726 to carry out drug data analytic and patient risk scoring processes that are arranged to perform functions as described herein including those described with respect to process 200 of FIG. 2 and process 300 of FIG. 3. Program data 724 may include drug-related casualty and patient data that may be useful for developing an abandoned patient model as is described herein. In some embodiments, application 722 may be arranged to operate with program data 724 on operating system 720 such that implementations of the abandoned patient model in, e.g., healthcare systems to assist clinicians in treating patients in clinical settings and post-examination or discharge, may be provided as described herein. This described basic configuration 702 is illustrated in FIG. 7 by those components within the inner dashed line.

Computing device 700 may have additional features or functionality, and additional interfaces to facilitate communications between basic configuration 702 and any required devices and interfaces. For example, a bus/interface controller 730 may be used to facilitate communications between basic configuration 702 and one or more data storage devices 732 via a storage interface bus 734. Data storage devices 732 may be removable storage devices 736, non-removable storage devices 738, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 706, removable storage devices 736 and non-removable storage devices 738 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 700. Any such computer storage media may be part of computing device 700.

Computing device 700 may also include an interface bus 740 for facilitating communication from various interface devices (e.g., output devices 742, peripheral interfaces 744, and communication devices 746) to basic configuration 702 via bus/interface controller 730. Example output devices 742 include a graphics processing unit 748 and an audio processing unit 750, which may be configured to communicate to various external devices such as a display or speakers via one or more A/V ports 752. Example peripheral interfaces 744 include a serial interface controller 754 or a parallel interface controller 756, which may be configured to communicate with external devices such as input devices (e.g., keyboard, mouse, pen, voice input device, touch input device, etc.) or other peripheral devices (e.g., printer, scanner, etc.) via one or more I/O ports 758. An example communication device 746 includes a network controller 760, which may be arranged to facilitate communications with one or more other computing devices 762 over a network communication link via one or more communication ports 764.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 700 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 700 may also be implemented as a personal computer including both laptop computer and non-laptop computer configurations.

In some embodiments presented herein, a data analysis may be utilized to identify patients at low risk of drug overdose, diversion, and/or addiction yet at risk of their current drug treatment dosages being reduced or eliminated in the response to efforts to curtail overall abuse of the drug in the general populace. The data analysis can identify these so-called "abandoned patients" and provide clinical insights relevant to the point-of-care that, in addition to helping these patients maintain their current successful treatment, allows for lower system costs and improved care and/or care delivery for subjects being successfully treated with a drug, individually or as part of a larger regimen, but misidentified as at risk for abuse of the drug. The approach may utilize a model that, once validated, can be integrated into hospital EHR and informatics systems to assist clinicians in treating patients in hospital settings as well as post-discharge. Indeed, integration and subject scoring can be automatically performed, the choice depending upon implementation at the particular institution. The direct impact of the scheme is a new way to identify those patients who are benefiting from their drug treatment and are thus not considered susceptible to abuse or in need of curtailment or cessation of treatment.

In one or more embodiments, some abandoned patients may have a consistent and/or regular history of successful pain management, for example outpatients who receive a stable dose of the same opioid over an extended period of time without appreciable side effects such as tolerance buildup or withdrawal symptoms during periods off treatment. Such patients are well served by maintaining their treatment regimens despite aggressive efforts to cut back or remove their drugs from public use. Changing their treatments in the name of stopping a public scourge may be considered abandoning them to their pain. A targeted model may enable clinicians, patient-family members, and caregivers to identify patients at high risk of abandonment and at low risk of a drug abuse disorder, such as those who may need and truly benefit from opioid medication either to manage long-term, chronic pain, or intense, episodic pain. The above-described model may leverage informatics to identify these individuals and suggest steps that can be taken that outreach can be made to these patients before abandonment.

In this description a number of possible data sources are mentioned. Such sources should not be considered limiting. Other examples of information from disparate data sources may include:

Health system data, including but not limited to:
  Readmission data
  Service lines
  Capacity levels
  Clinician notes
  Discharge summaries
  Drug prescriptions written/filled
  Facility location
  Claims data
  Global budget data
ER utilization:
  Readmission rates
  Patient characteristics
Health Data Sets, including but not limited to:
  Electronic health records (EHR) systems
  Electronic medical records (EMR) systems
  Aggregated health data sets of acquired hospital and patient records
Law Enforcement data, including but not limited to:
  Overdose locations (as reported by police, fire, EMS)
  Drug-related crime rates These headings are provided for illustration and conciseness, and should not be considered limiting to the extent of the elements listed. Likewise, inclusion under a specific heading does not imply that any of the listed elements must belong exclusively in the list or with the heading under which it appears.

The foregoing description is presented to enable one of ordinary skill in the art to make and use the disclosed embodiments and modifications thereof, and is provided in the context of a patent application and its requirements. Various modifications to the disclosed embodiments and the principles and features described herein will be readily apparent to those of ordinary skill in the art. Thus, the present disclosure is not intended to limit the invention to the embodiments shown; rather, the invention is to be accorded the widest scope consistent with the principles and features described herein.

What is claimed is:

1. A method to evaluate a patient's risk of drug treatment change due to a category misidentification, comprising:
   generating a predictive model for evaluating the patient's risk of drug treatment change, wherein the predictive model includes a plurality of analyzer channels to customize or fine tune the predictive model,
     wherein the generating of the predictive model includes training the predictive model by iteratively adjusting a weight of one or more of the plurality of analyzer channels until the predictive model passes the training to reduce the misidentification by the predictive model of the risk of drug treatment change by:
       acquiring data of a subject population (X) by extracting the data from one or more data sources using at least natural language processing,
       identifying patients (Y) as a first subset of the subject population (X) based on at least one criterion,
       identifying patients (Z) as a second subset of the subject population (X) by producing a risk score of each individual in the subject population using the predictive model,
       determining a correlation between (Y) and (Z) for the patients' risk of drug abuse,
       determining whether the correlation between (Y) and (Z) at least meets a predetermined threshold,
       if the correlation does not at least meet the threshold, adjusting the weight for the one or more of the plurality of analyzer channels of the predictive model to customize or fine tune the predictive model and repeating identifying patients (Z), determining a correlation between (Y) and (Z), and determining whether the correlation at least meets a predetermined threshold in accordance with the adjustments, if the correlation at least meets the threshold, outputting the predictive model by incorporating the predictive model in a healthcare records system;

applying the predictive model to data of a patient;

determining a patient risk score for the patient being misidentified as being at risk of abusing a drug used in the drug treatment based on a result of the applying the predictive model to the data of the patient;

not reducing or cancelling an amount of the drug treatment based on the patient risk score, when the patient is misidentified as being at risk of abusing the drug and is benefiting from the drug treatment.

2. The method of claim 1, wherein the subject population (X) is victims of drug overdose, attempted suicide, and fatal suicide.

3. The method of claim 2, wherein, in accordance with the model, the patients (Z) are identified as individuals in the subject population (X) who are or were undergoing treatment with a drug and misidentified as being at risk for abuse of the drug.

4. The method of claim 3, wherein the risk for abuse of the drug is one or more of drug addiction, diversion of prescribed drugs, and drug overdose.

5. The method of claim 4, wherein the drug is an opioid.

6. The method of claim 1,
wherein the model includes structured and unstructured information;
wherein the unstructured information includes health system data; and
wherein outputting the adjusting the model includes feeding the adjusted model back to the healthcare records system.

7. The method of claim 1, wherein the at least one criterion includes long-term pain management treatment which was one of tapered off or discontinued.

8. A method to evaluate a patient's risk of drug treatment change due to a category misidentification, comprising:
generating a predictive model for evaluating the patient's risk of drug treatment change, wherein the predictive model includes a plurality of analyzer channels to customize or fine tune the predictive model,
wherein the generating of the predictive model includes training the predictive model by iteratively adjusting a weight of one or more of the plurality of analyzer channels until the predictive model passes the training to reduce the misidentification by the predictive model of the risk of drug treatment change by:
acquiring data of a subject population (X) by extracting the data from one or more data sources using at least natural language processing,
identifying patients (Y) as a first subset of the subject population (X) based on at least one criterion,
identifying patients (Z) as a second subset of the subject population (X) by producing a risk score of each individual in the subject population using the predictive model,
determining a correlation between (Y) and (Z) for the patients' risk of drug abuse,
determining whether the correlation between (Y) and (Z) at least meets a predetermined threshold,
if the correlation does not at least meet the threshold, adjusting the weight for one or more of the plurality of analyzer channels of the predictive model to customize or fine tune the predictive model and repeating identifying patients (Z), determining a correlation between (Y) and (Z), and determining whether the correlation at least meets a predetermined threshold in accordance with the adjustment,
if the correlation at least meets the threshold, outputting the predictive model; applying the predictive model to data of a patient;
determining a patient's risk of abuse of a painkilling drug using the applied predictive model to determine whether the patient's risk of abuse of the painkilling drug is relatively high or relatively low based on a standard;
if the patient's risk of abuse of the painkilling drug is determined to be relatively low, indicating referral of the patient for treatment with the painkilling drug;
wherein the determining the patient's risk of abuse includes determining a patient risk score for the patient being misidentified as being at risk of abusing a drug used in the drug treatment based on a result of the applying the predictive model to the data of the patient in which the patient's risk of abuse is relatively low based on a lower patient risk score;
not reducing or cancelling an amount of the painkilling drug based on the patient risk score, when the patient is misidentified as being at risk of abusing the drug and is benefiting from the drug treatment.

9. The method of claim 8, further comprising:
adjusting the model based on feedback from the treatment.

10. The method of claim 9,
wherein the model includes structured and unstructured information;
wherein the unstructured information includes a clinician's notes; and
wherein adjusting the model includes feeding the adjusted model back to the healthcare records system.

11. The method of claim 8, wherein the risk of abuse of the drug is one or more of drug addiction, diversion of prescribed drugs, and drug overdose.

12. The method of claim 11, wherein the drug is an opioid.

13. A non-transitory computer-readable medium having computer-readable instructions that, if executed by a computing device, cause the computing device to perform operations comprising:
generating a predictive model for evaluating the patient's risk of drug treatment change, wherein the predictive model includes a plurality of analyzer channels to customize or fine tune the predictive model,
wherein the generating the predictive model includes training the predictive model by iteratively adjusting a weight of one or more of the plurality of analyzer channels until the predictive model passes the training to reduce the misidentification by the predictive model of the risk of drug treatment change by:
acquiring data of a population (X) by extracting the data from one or more data sources using at least natural language processing,
identifying patients (Y) as a first subset of population (X) based on at least one criterion,
identifying patients (Z) as a second subset of population (X) by producing a risk score of each individual in the subject population using the predictive model,
determining a correlation between (Y) and (Z) for the patients' risk of drug abuse, determining whether the correlation between (Y) and (Z) at least meets a predetermined threshold, if the correlation does not at least meet the threshold, adjusting the weight for one or more of the plurality of analyzer channels of the predictive model to customize or fine tune the predictive model and repeating identifying patients (Z), determining a correlation between (Y) and (Z), and determining whether the correlation at least meets a predetermined threshold in accordance with the adjustment, if the correlation at least meets the threshold, outputting the predictive model by incorporating the predictive model into a healthcare records system;

applying the predictive model to data of a patient;

determining a patient risk score for the patient being misidentified as being at risk of abusing a drug used in the drug treatment based on a result of the applying the predictive model to the data of the patient;

not reducing or cancelling an amount of the drug treatment based on the patient risk score, when the patient is misidentified as being at risk of abusing the drug and is benefiting from the drug treatment.

14. The non-transitory computer-readable medium of claim 13, wherein the subject population (X) is victims of drug overdose, attempted suicide, and fatal suicide.

15. The non-transitory computer-readable medium of claim 13, wherein, in accordance with the model, the patients (Z) are identified as individuals in the subject population (X) who are or were undergoing treatment with a drug and at low risk for abuse of the drug.

16. The non-transitory computer-readable medium of claim 13, wherein the risk for abuse of the drug is one or more of drug addiction, diversion of prescribed drugs, and drug overdose.

17. The non-transitory computer-readable medium of claim 13, wherein the drug is an opioid.

18. The non-transitory computer-readable medium of claim 13, wherein the model includes structured and unstructured information;

wherein the unstructured information includes a clinician's notes; and wherein outputting the adjusting the model includes feeding the adjusted model back to the clinician's electronic health records system.

* * * * *